United States Patent [19]

Nohira et al.

[11] Patent Number: 5,075,031
[45] Date of Patent: Dec. 24, 1991

[54] MESOMORPHIC COMPOUND AND LIQUID CRYSTAL COMPOSITION CONTAINING THE SAME

[75] Inventors: Hiroyuki Nohira, Saitama; Takashi Kimura, Tochigi; Yoko Yamada, Kanagawa; Kazushige Yamagishi, Shiga, all of Japan

[73] Assignee: Canon Kabushiki Kaisha, Tokyo, Japan

[21] Appl. No.: 456,198

[22] Filed: Dec. 20, 1989

Related U.S. Application Data

[63] Continuation of Ser. No. 269,617, Nov. 10, 1988, abandoned.

[30] Foreign Application Priority Data

Nov. 12, 1987 [JP]  Japan ................... 62-284251
Feb. 24, 1988 [JP]  Japan ................... 63-039459

[51] Int. Cl.$^5$ .................. C09K 19/34; C09K 19/12; C07D 239/02; C07C 255/00
[52] U.S. Cl. .................. 252/299.61; 252/299.63; 252/299.65; 252/299.66; 252/299.67; 544/298; 544/301; 544/316; 544/335; 558/389; 558/398; 558/399; 558/426; 558/430; 359/104
[58] Field of Search .................. 252/299.01, 299.61, 252/299.63, 299.65, 299.66, 299.67; 350/350 R, 350 S; 544/298, 316, 335, 242, 301; 558/354, 398, 399, 389, 426, 430

[56] References Cited

U.S. PATENT DOCUMENTS

| 4,576,732 | 3/1986 | Isogai et al. ............ 252/299.67 |
| 4,592,856 | 6/1986 | Higuchi et al. .......... 252/299.66 |
| 4,613,209 | 9/1986 | Goodby et al. .......... 252/299.67 |
| 4,695,650 | 9/1987 | Walba et al. ............ 252/299.67 |
| 4,723,005 | 2/1988 | Huynh-Ba et al. ...... 252/299.63 |
| 4,725,688 | 2/1988 | Taguchi et al. ......... 252/299.61 |
| 4,728,458 | 3/1988 | Higuchi et al. .......... 252/299.67 |
| 4,732,699 | 3/1988 | Higuchi et al. .......... 252/299.66 |
| 4,777,280 | 10/1988 | Eidman et al. ......... 252/299.67 |
| 4,786,730 | 11/1988 | Shibata et al. .......... 252/299.61 |
| 4,798,680 | 1/1989 | Nohira et al. ........... 252/299.01 |
| 4,820,939 | 4/1989 | Krause et al. ........... 252/299.61 |

FOREIGN PATENT DOCUMENTS

| 239444 | 9/1987 | European Pat. Off. ........ 252/299.64 |
| 248335 | 12/1987 | European Pat. Off. ........ 252/299.61 |
| 3525015 | 1/1986 | Fed. Rep. of Germany ........ 252/299.66 |
| 3515373 | 11/1986 | Fed. Rep. of Germany ........ 252/299.61 |
| 3638026 | 11/1986 | Fed. Rep. of Germany . |
| 63-22042 | 1/1988 | Japan ...................... 252/299.01 |
| 63-104949 | 4/1988 | Japan ...................... 252/299.01 |
| 03530 | 5/1988 | PCT Int'l Appl. . |
| 04290 | 6/1988 | PCT Int'l Appl. . |
| 2166754 | 5/1986 | United Kingdom . |
| 8705018 | 8/1987 | World Int. Prop. O. ....... 252/299.01 |
| 8706021 | 10/1987 | World Int. Prop. O. ....... 252/299.01 |
| 8705017 | 8/1988 | World Int. Prop. O. ....... 252/299.01 |
| 8808019 | 10/1988 | World Int. Prop. O. ....... 252/299.61 |

Primary Examiner—John S. Maples
Assistant Examiner—Philip Tucker
Attorney, Agent, or Firm—Fitzpatrick, Cella, Harper & Scinto

[57] ABSTRACT

A mesomorphic compound represented by the formula:

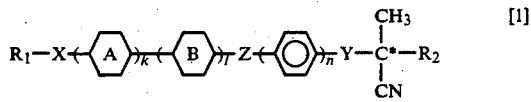

wherein $R_1$ denotes an alkyl group having 1–16 carbon atoms; $R_2$ denotes an alkyl group having 2–10 carbon atoms; X denotes a single bond or —O—; Y denotes —OCH$_2$—,

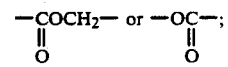

Z denotes a single bond,

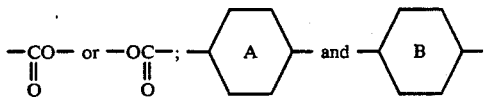

respectively and independently denote

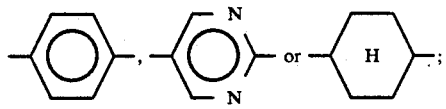

k, l and n are respectively 0, 1 or 2 satisfying the relation of k+l+n=2 or 3; C* denotes an asymmetric carbon atom. The mesomorphic compound, when added as a component, provides a liquid crystal composition showing an improved field respective characteristic or is effective in preventing occurrence of a reverse domain.

25 Claims, No Drawings

MESOMORPHIC COMPOUND AND LIQUID CRYSTAL COMPOSITION CONTAINING THE SAME

This application is a continuation of application Ser. No. 269,617, filed Nov. 10, 1988, now abandoned.

FIELD OF THE INVENTION AND RELATED ART

The present invention relates to a novel mesomorphic compound, a liquid crystal composition containing the same and a liquid device using the liquid crystal composition.

There has been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127-128. In this type of liquid crystal devices, the number of picture elements have been restricted, because there is a problem that a crosstalk phenomenon occurs when a device of a matrix electrode structure with a high density of picture elements is driven according to a multiplexing driving scheme. Further, their uses for display have been limited because of slow electric field response and poor visual angle characteristics.

As another type of liquid crystal device, there has been known one comprising a plurality of picture elements each connected to and subject to switching by a then film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924). As the bistable liquid crystal, a ferroelectric liquid crystal showing a chiral smectic C phase (SmC*) or H phase (SmC*) is generally used.

Such a ferroelectric liquid crystal has very rapid response speed on account of having spontaneous polarization, can also exhibit memorizable bistable state and further have excellent vision angle characteristic and therefore it is suitable for a display of large capacity and large picture area.

Further, since a material used as a ferroelectric liquid crystal has an asymmetry, it can be used as a functional material to be used in the following types of optical devices in addition to the use as a ferroelectric liquid crystal material:

1) Those utilizing a cholesteric-nematic phase transition in a liquid crystal state (J. J. Wysoki, A. Adams and W. Hass: Phys. Rev. Lett., 20, 10204 (1968);

2) Those utilizing a guest-host effect of the White-Taylor type in a liquid crystal state (D. L. White and G. N. Taylor: J. Appl. Phys. 45, 4718 (1974)).

These optical devices are important as display devices and modulation devices, while the explanation of the individual systems is left to the respective references and omitted.

It has been understood that, in a method utilizing an electric field-responsive optical effect of a liquid crystal, it is desirable to introduce a polar group or a group providing a polar bond in a compound constituting the liquid crystal in order to enhance the responsive characteristic of the liquid crystal. Particularly, with respect to a ferroelectric liquid crystal, it has been known that the responsive speed is proportional to its spontaneous polarization, so that it is desired to increase the spontaneous polarization in order to realize a high response speed. From this viewpoint, P. Keller et al have shown that it is possible to provide a higher response speed by introducing a chlorine atom directly connected to an asymmetric carbon atom. However, such a chlorine atom directly introduced to an asymmetric carbon atom involves problems that it is chemically unstable and lowers the stability of a liquid crystal phase as it has a large atomic radius.

On the other hand, many of optically active functional compounds for use in optical devices as described above are synthesized through an intermediate which per se is optically active. Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives. However, it has been seldom to incorporate a polar group into such an intermediate. Partly for this reason, the above mentioned method of introducing a polar group directly to an asymmetric carbon atom has not been utilized very effectively.

SUMMARY OF THE INVENTION

A principal object of the present invention is, in view of the above problems, to provide a mesomorphic compound having an enhanced electric field-responsive characteristic in an liquid crystal state by introducing a fluorine atom, which is stable and has a large dipole moment, directly to an asymmetric carbon atom.

Another object of the present invention is to provide a liquid crystal composition comprising at least one species of the mesomorphic compound.

A further object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146 (1964), and a liquid crystal composition containing at least one species of the mesomorphic compound.

According to the present invention, there is provided a mesomorphic compound represented by the formula:

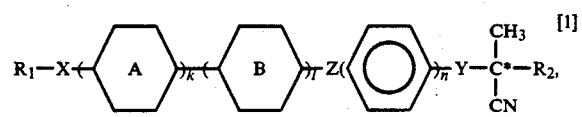

wherein $R_1$ denotes an alkyl group having 1-16 carbon atoms; $R_2$ denotes an alkyl group having 2-10 carbon atoms; X denotes a single bond or —O—; Y denotes —OCH$_2$—,

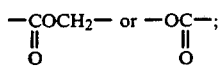

Z denotes a single bond,

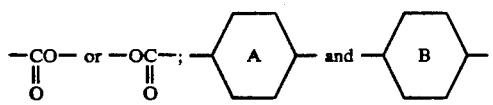

respectively and independently denote

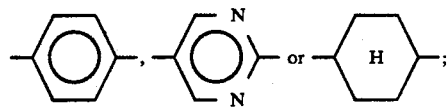

k, l and n are respectively 0, 1 or 2 satisfying the relation of k+l+n=2 or 3; C* denotes an asymmetric carbon atom.

According to the present invention, there is further provided a liquid crystal composition containing at least one species of the above mentioned mesomorphic compound.

The present invention further provides a liquid crystal device using the liquid crystal composition.

These and other objects, features and advantages of the present invention will become more apparent upon a consideration of the following description of the preferred embodiments of the present invention.

DETAILED DESCRIPTION OF THE INVENTION

The mesomorphic compound represented by the above-mentioned formula [1] of the present invention may preferably be synthesized from an optically active intermediate represented by the following formula [2] developed by our research group and disclosed in Japanese Patent Application Nos. 283079/1987 and 38617/1988:

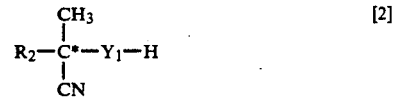

wherein $R_2$ denotes an alkyl group having 2–10 carbon atoms; $Y_1$ denotes

or —CH$_2$O—; and C* denotes an asymmetric carbon atom.

The reaction schemes are summarized hereinbelow:

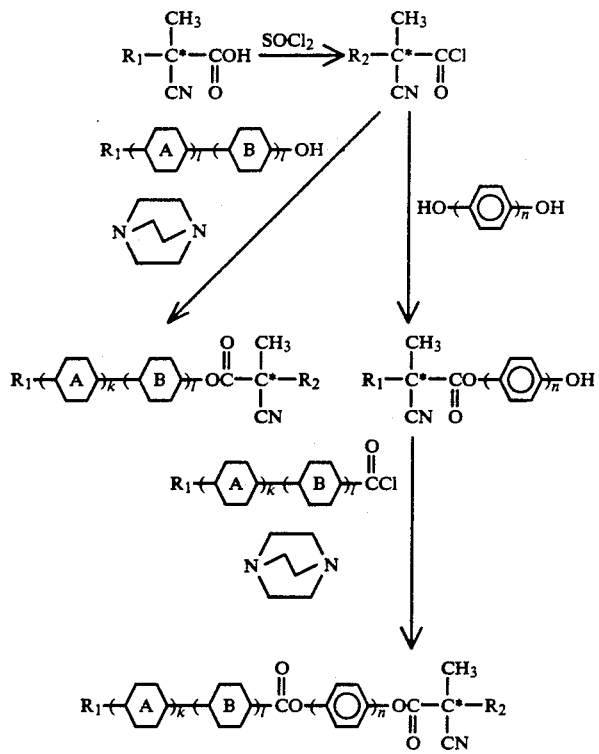

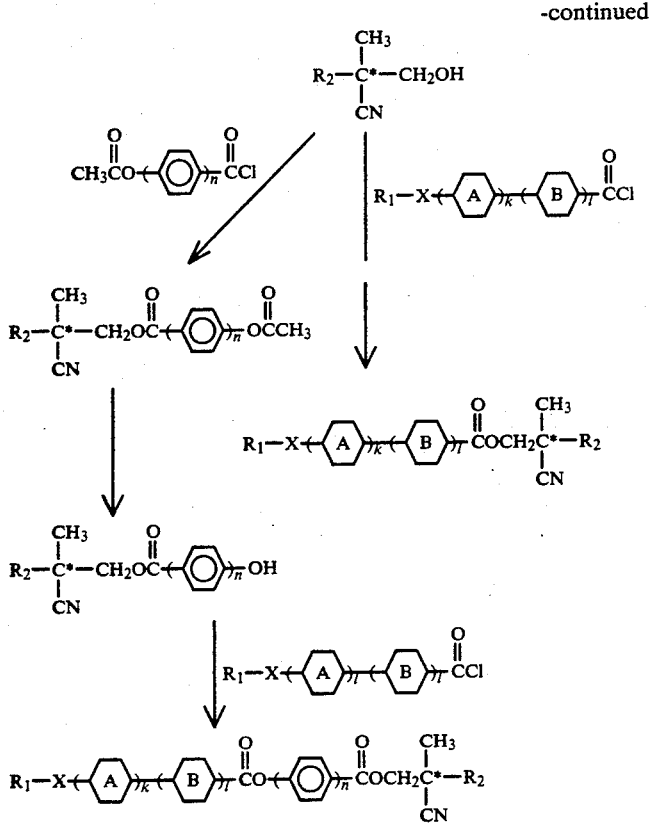
③ Case where —Y— is —OCH$_2$—
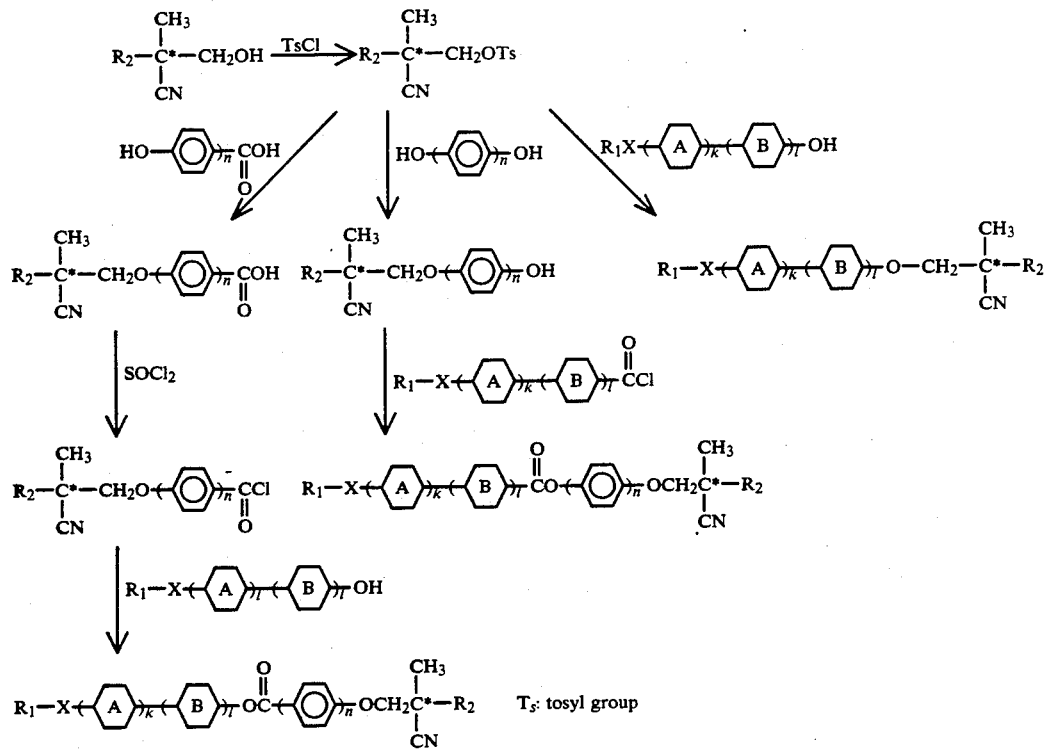
T$_s$: tosyl group
Herein, R$_1$, R$_2$,

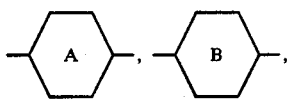
k, l and n are the same as defined above.
Some representative examples of the compound represented by the general formula [1] are enumerated hereinbelow:
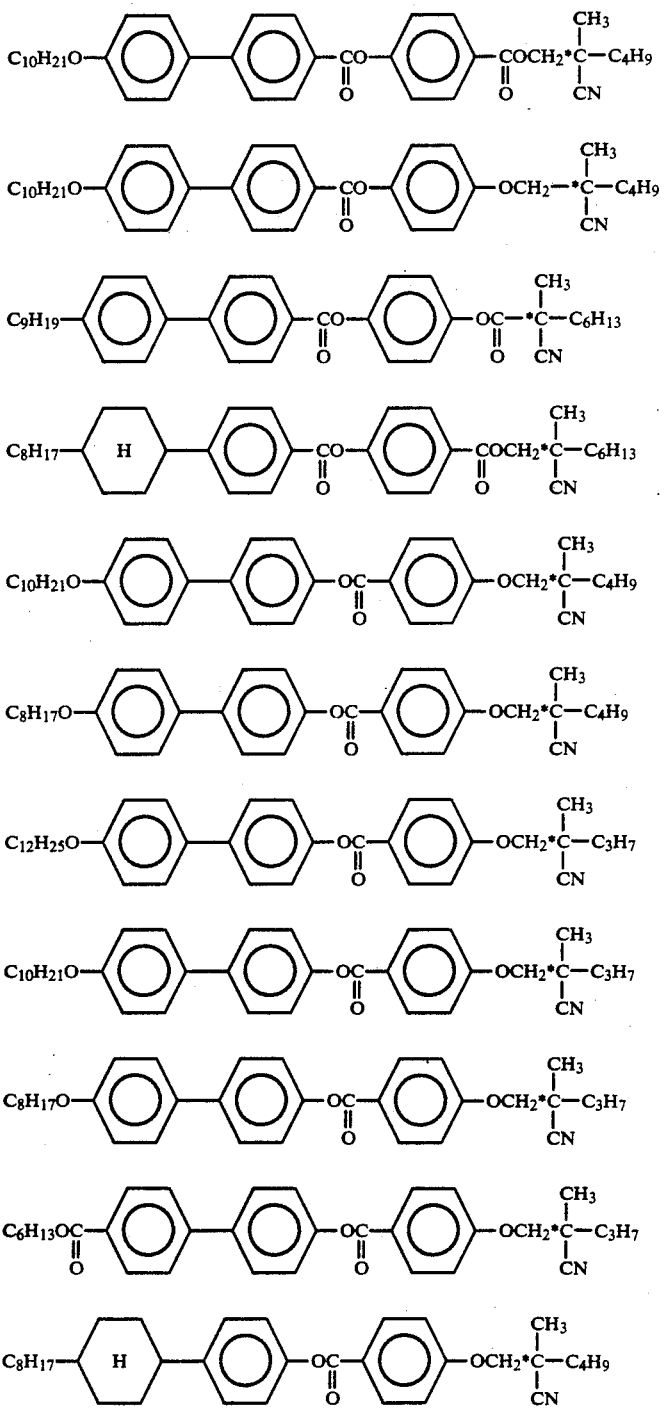

-continued
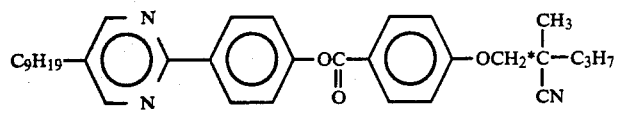
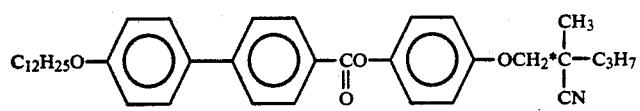
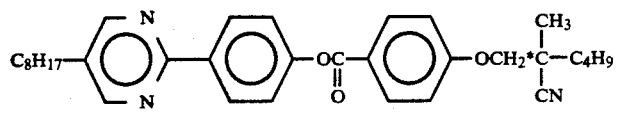
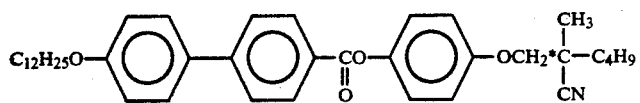
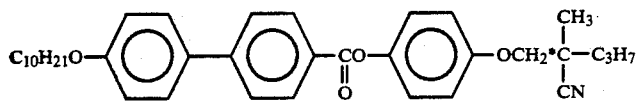
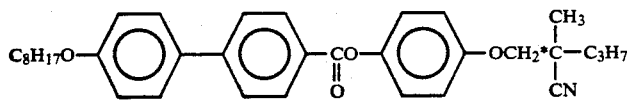
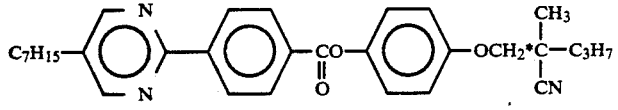
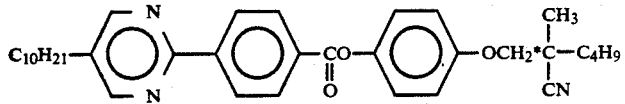
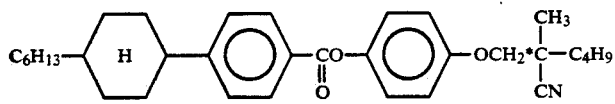
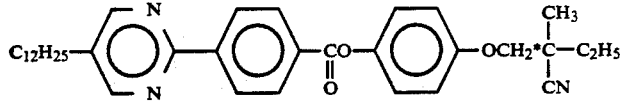
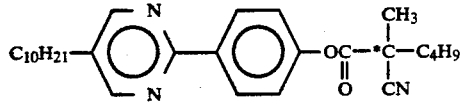
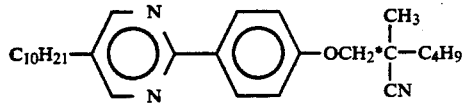
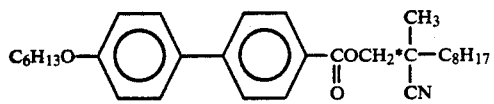

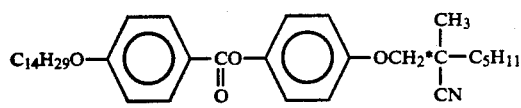
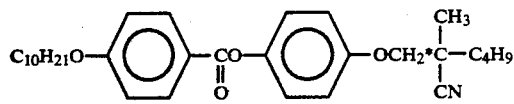
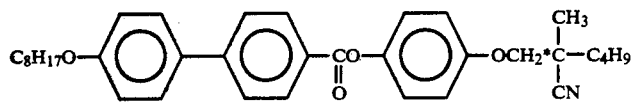
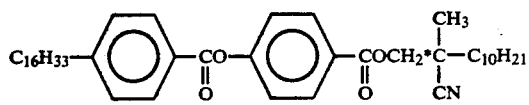
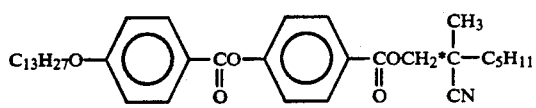

The liquid crystal composition according to the present invention contains at least one species of the mesomorphic compound represented by the formula [1]. For example, the mesomorphic compound represented by the formula [1] may be mixed with a ferroelectric liquid crystal selected from those of the formulas (1)–(13) shown below to increase the spontaneous polarization and increase the response speed. In this case, it is preferred to use the mesomorphic compound represent by the formula [1] in an amount constituting 0.1–99 wt. %, particularly 1–90 wt. %, of the resulting liquid crystal composition.

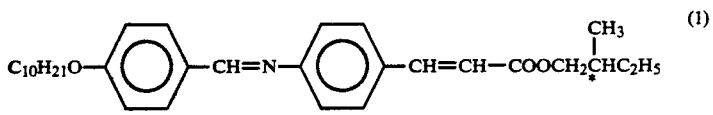 (1)

p-decyloxybenzylidene-p'-amino-2-methylbutylcinnamate (DOBAMBC)

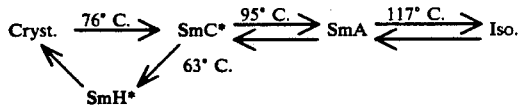

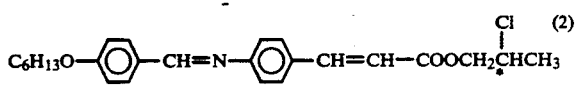 (2)

p-hexyloxybenzylidene-p'-amino-2-chloropropylcinnamate (HOBACPC)

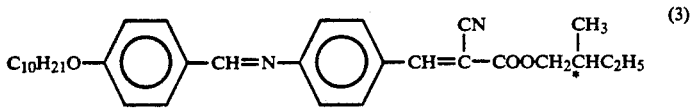 (3)

p-decyloxybenzylidene-p'-amino-2-methylbutyl-α-cyanocinnamate (DOBAMBCC)

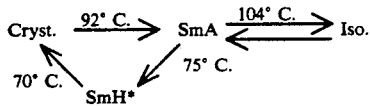

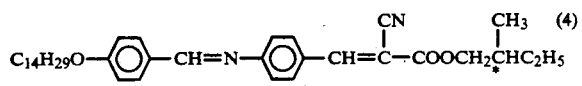 (4)

p-tetradecyloxybenzylidene-p'-amino-2-methylbutyl-α-cyanocinnamate (TDOBAMBCC)

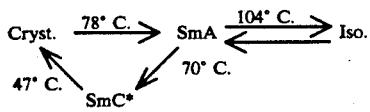

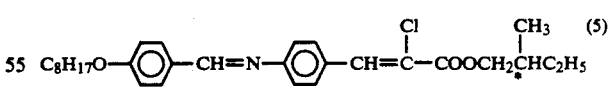 (5)

p-octyloxybenzylidene-p'-amino-2-methylbutyl-α-chlorocinnamate (OOBAMBCC)

Cryst. $\xrightleftharpoons{41° C.}$ SmA $\xrightleftharpoons{66° C.}$ Iso (6)
27° C. ↖ ↙ 38° C.
SmC*

C₈H₁₇O—⟨phenyl⟩—CH=N—⟨phenyl⟩—CH=C(CH₃)—COOCH₂CH(*)C₂H₅ with CH₃ p-octyloxybenzylidene-p′-amino-2-methylbutyl-α-methylcinnamate

Cryst. $\xrightleftharpoons{49° C.}$ SmC* $\xrightleftharpoons{58° C.}$ SmA $\xrightleftharpoons{94° C.}$ Iso.

C₂H₅CH(CH₃)CH₂OCO—CH=CH—⟨phenyl⟩—N=N(→O)—⟨phenyl⟩—CH=CHCOOCH₂CH(CH₃)C₂H₅

4,4′-azoxycinnamic acid-bis(2-methylbutyl)ester

Cryst. $\xrightleftharpoons{121° C.}$ SmC* $\xrightleftharpoons{134° C.}$ SmA $\xrightleftharpoons{168° C.}$ Iso. (8)

C₂H₅CH(CH₃)CH₂O—⟨phenyl-OH⟩—CH=N—⟨phenyl⟩—C₈H₁₇

4-O-(2-methylbutyl)resorcylidene-4′-octylaniline (MBRA 8)

Cryst. $\xrightleftharpoons{28° C.}$ SmC* $\xrightleftharpoons{55° C.}$ SmA $\xrightleftharpoons{62° C.}$ Iso. (9)

C₈H₁₇O—⟨phenyl⟩—⟨phenyl⟩—COO—⟨phenyl⟩—CH₂CH(*)(CH₃)C₂H₅

4-(2′-methylbutyl)phenyl-4′-octyloxybiphenyl-4-carboxylate

Cryst. $\xrightleftharpoons{78° C.}$ Sm3 $\xrightleftharpoons{80° C.}$ SmC* $\xrightleftharpoons{128.3° C.}$ SmA $\xrightleftharpoons{170° C.}$ Ch $\xrightleftharpoons{174.2° C.}$ Iso.

C₂H₅CH(*)(CH₃)CH₂—⟨phenyl⟩—⟨phenyl⟩—COO—⟨phenyl⟩—OC₆H₁₃

4-hexyloxypenyl-4-(2″-methylbutyl)biphenyl-4′-carboxylate

Cryst. $\xrightleftharpoons{68.8° C.}$ SmC* $\xrightleftharpoons{80.2° C.}$ Ch. $\xrightleftharpoons{163.5° C.}$ Iso. (11)

C₂H₅CH(*)(CH₃)CH₂—⟨phenyl⟩—⟨phenyl⟩—COO—⟨phenyl⟩—OC₈H₁₇

4-octyloxyphenyl-4-(2″-methylbutyl)biphenyl-4′-carboxylate (12)

Cryst. $\xrightleftharpoons{78° C.}$ SmC* $\xrightleftharpoons{88.6° C.}$ Ch. $\xrightleftharpoons{155.4° C.}$ Iso.

C₂H₅CH(CH₃)(CH₂)₃—⟨phenyl⟩—⟨phenyl⟩—COO—⟨phenyl⟩—C₇H₁₅

4-heptylphenyl-4-(2″-methylbutyl)biphenyl-4′-carboxylate

Cryst. $\xrightleftharpoons{91.5° C.}$ SmC* $\xrightleftharpoons{93° C.}$ Sma $\xrightleftharpoons{112° C.}$ Ch. $\xrightleftharpoons{131° C.}$ Iso. (13)

C₂H₅CH(CH₃)(CH₂)₃—⟨phenyl⟩—⟨phenyl⟩—COO—⟨phenyl⟩—CH₂CH(CH₃)C₂H₅

4-(2″-methylbutyl)phenyl-4-(4″-methylhexyl)biphenyl-4″-carboxylate

Cryst. $\xrightarrow{83.4° C.}$ Ch. $\xrightarrow{114° C.}$ Iso.
↓ 81.0° C.
SmC* $\xleftarrow{74.3° C.}$ SmA Herein, the symbols used for describing phase-transition respectively denote the following phases.
Cryst.: crystal phase,
SmA: smectic A phase,
SmC*: chiral smectic phase,
N: nematic phase,
Ch.: cholesteric phase,
Iso.: isotropic phase, SmA: smectic A phase,
SmB: smectic B phase, and
Sm3: smectic phase (un-identified) other than SmA and SmC*.

The mesomorphic compound represented by the formula [1] may also be mixed with a smectic liquid crystal such as those of the formulas (14)–(18) below which per se are not chiral to provide a composition which may be used as a ferroelectric liquid crystal. In this case, the mesomorphic compound represented by the formula [1] may preferably be used in an amount of 0.1–99 wt. %, particularly 1–90 wt. %. The resultant composition may be provided with an increased spontaneous polarization corresponding to the content of the mesomorphic compound according to the present invention.

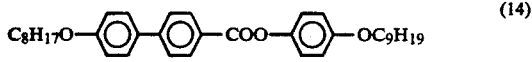
(14)

(4-nonyloxyphenyl)-4'-octyloxybiphenyl-4-carboxylate

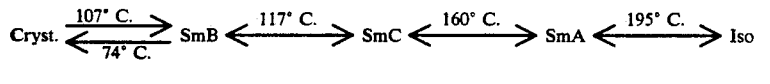

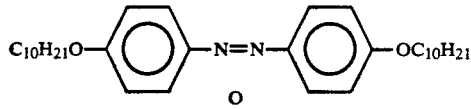

4,4'-decyloxyazoxybenzene

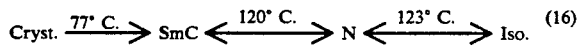
(16)

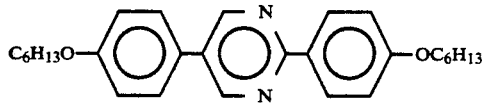

2-(4'-hexyloxyphenyl)-5-(4-hexyloxyphenyl)pyrimidine

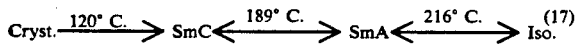
(17)

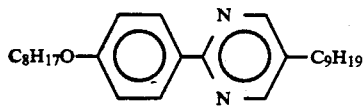

2-(4'-octyloxyphenyl)-5-nonylpyrimidine

(18)

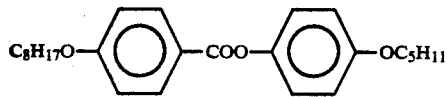

4'-pentyloxyphenyl-4-octylazoxybenzoate

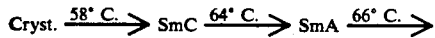

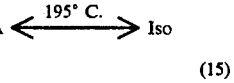

Hereinbelow, the present invention will be explained more specifically with reference to some examples.

EXAMPLE 1

2-cyano-2-methylhexyl p-(p-decyloxybiphenylcarbonyloxy)benzoate was synthesized through the following steps 1), 2) and 3).

Step 1

Synthesis of 2-cyano-2-methylhexyl p-acetoxybenzoate.

360 mg (2 mM) of acetoxybenzoic acid and 4 ml of thionyl chloride were heat-refluxed for 2 hours, followed by distilling-off of excessive thionyl chloride under reduced pressure to form an acid chloride, to which was added a solution of 282 mg (2 mM) and 448 mg (4 mM) of triethylenediamine in 5 ml of benzene.

The mixture was stirred under heating at 50° C. for 2 hours, followed by addition of a solution of 94 mg (4 mM) of sodium hydride in 2 ml of dry benzene and 2 hours of heat-refluxing. After the reaction, the mixture was left standing at room temperature for cooling, and 8 ml of 1N-hydrochloric acid and 20 ml of distilled water were added thereto. The organic layer was separated, the aqueous layer was extracted by ether, and the ether extract was added to the organic layer. The organic mixture was washed with distilled water and dried on sodium sulfate, followed by distilling-off of the solvent and purification by thin layer chromatography (developer solvent: ethyl acetate/methylene chloride=1:14) to obtain 345 mg of optically active 2-cyanomethylhexyl p-acetoxybenzoate (Yield: 56.9%).

Step 2

Synthesis of 2-cyano-2-methylhexyl p-hydroxybenzoate.

482 mg (1.6 mM) of 2-cyano-2-methylhexyl p-acetoxybenzoate obtained in Step 1) was dissolved in 1.5 ml of dry ether, and a solution of 188 mg (1.6 mM) of benzylamine in 1 ml of ether was added thereto, followed by 24 hours of stirring at room temperature. After the reactions and distilling-off of the solvent, the product was purified by thin layer chromatography (developer solvent: ethyl acetate/methylene chloride=1:5) to obtain 339 mg of 2-cyano-2-methylhexyl p-hydroxybenzoate (yield 73.7%).

Step 3

Synthesis of 2-cyano-2-methylhexyl p-(p-decyloxybiphenylcarbonyloxy)benzoate.

211 mg (1.18 mM) of decyloxybiphenylcarboxylic acid and 2.5 ml of thionyl chloride were heat-refluxed for 2 hours, followed by distilling-off of excessive thionyl chloride. To the resultant acid chloride was added a solution of 339 mg (1.18 mM) of 2-cyano-2-methylhexyl p-hydroxybenzoate and 263 mg (2.36 mM) of thiethylenediamine in 5 ml of dry benzene, followed by 2 hours of stirring under heating at 50° C. Then, a solution of 56.5 mg (2.36 mM) of sodium hydride in 2 ml of dry benzene was added, followed by 2 hours of heat-refluxing. After the reaction, the mixture was cooled to room temperature, followed by addition of 5 ml of 1N-hydrochloric acid and 12 ml of distilled water and extraction with ether. The ether solution was dried on sodium sulfate, followed by distilling-off of the solvent and purification by thin layer chromatography (developer solvent: benzene/methylene chloride=1:3) to obtain 230 mg of 2-cyano-2-methylhexyl p-(p-decyloxybiphenyl carbonyloxy)benzoate. Yield: 32.1%. $[\alpha]_D$ −4.6 degrees (c1, methylene chloride). Phase transition temperatures (°C.):

EXAMPLE 2

Synthesis of p-(5-n-decyl-2-pyrimidyl)phenyl 2-cyano-2-methylhexanoate.

155 mg (1 mM) of (−)-2-cyano-2-methylhexanoic acid ($[\alpha]_D$ −6.15 degrees (c1, methanol)) and 2 ml of thionyl chloride were placed in a dried flask and heat-refluxed in a nitrogen atmosphere, followed by distilling-off of excessive thionyl chloride under reduced pressure. To the resultant acid chloride was added a solution of 312 ml (1 mM) of 4-(5-n-decyl-2-pyrimidyl)-phenol and 240 mg (2 mM) of triethylenediamine in 2.5 ml of dry benzene, followed by 2 hours of reaction at 50° C. Further, a solution of 80 mg (2 mM) of sodium hydride in dry benzene was added thereto, followed by 2 hours of reactions. After the reaction, the mixture was cooled to room temperature, followed by addition of 1N-hydrochloric acid and distilled water and extraction with ether. The resultant ether layer was dried on sodium sulfate, followed by distilling-off of the solvent and purification by thin layer chromatography (developer solvent: methylene chloride) to obtain 59 mg of p-(5-n-decyl-2-pyrimidyl)phenyl 2-cyano-2-methylhexanoate. Yield: 11.3% $[\alpha]_D$ −3.5 degrees (c1, methylene chloride) m.p.=38°-43° C.

EXAMPLE 3

4-(5-n-decyl-2-pyrimidyl)phenyl 2-cyano-2-methylhexyl ether was synthesized through the following steps 1) and 2).

Step 1

Synthesis of 2-cyano-2-methylhexyl p-toluenesulfonate.

535 mg (3.8 mM) of (+)-2-cyano-2-methylhexanol ($[\alpha]_D^{26}$ +0.66 degree (c 1.823, ether)) and 911 mg (11.4 mM) of dry pyridine were stirred at room temperature, and 724 mg (3.8 mM) of p-toluenesulfonyl chloride was added thereto, followed by 7 hours of reaction. After the reaction, 3 ml of 2N-hydrochloric acid was added thereto, followed by extraction with diethyl ether. the resultant organic layer was washed with a small amount of 2N-hydrochloric acid and distilled water, followed by drying on sodium sulfate, distilling-off of the solvent and purification by silica gel column chromatography (developer solvent: methylene chloride) to obtain 748 mg of 2-cyano-2-methylhexyl p-toluenesulfonate (yield: 63.3%).

Step 2

Synthesis of 4-(5-n-decyl-2-pyrimidyl)phenyl 2-cyano-2-methylhexyl ether.

28 mg (0.7 mM) of sodium hydride and 1.5 ml of dimethylformamide were stirred, and 220 mg (0.7 mM) of p-(5-n-decyl-2-pyrimidyl)phenol was added, followed by stirring for 10 minutes. Further, 218 mg (0.7 mM) of 2-cyano-methylhexyl p-toluenesulfonate and dimethylformamide were added, followed by 6 hours of stirring under heating at 100° C. After the reaction, the solvent was distilled off and distilled water was added thereto, followed by extraction with diethyl ether. The organic layer was washed with distilled water and dried on sodium sulfate. After distilling off the solvent, the product was purified by thin layer chromatography (developer solvent: hexane/methylene chloride=1/5) to obtain 149 mg of 4-(5-n-decyl-2-pyrimidyl)-phenyl 2-cyano-2-methylhexyl ether. Yield: 48.8%, $[\alpha]^{25}_D$ −1.47 (C 1.494, methylene chloride) m.p.: 43° C.

EXAMPLE 4

(−)-4-(4'-n-decyloxyphenyl)benzoic acid 4-(2'-cyano-2'-methylhexyloxy)phenyl ester was prepared through the following reaction steps 1), 2) and 3).

Step 1

Synthesis of (+)-2-cyano-2-methylhexyl p-toluenesulfonate.

535 mg (3.8 mM) of (−)-2-cyano-2-methylhexanol ($[\alpha]_{435}$ −1.9 degree (c=2.393, methylene chloride)) and 911 mg (11.4 mM) of dry pyridine were stirred at room temperature, followed by addition of 724 mg (3.8 mM) of p-toluenesulfonyl chloride and 7 hours of reaction. After the reaction, 6 ml of 2M-hydrochloric acid was added and extraction with ether was effected. The organic layer was washed with a small amount of 2M-hydrochloric acid and distilled water, followed by drying on sodium sulfate and distilling-off of the solvent under reduced pressure The product was then purified by thin layer chromatography (developer solvent: hexane/methylene chloride=1/5) to obtain 748 mg of (+) 2-cyano-2-methylhexyl p-toluenesulfonate. Yield: 63.3%, $[\alpha]_D$ +10.7 degrees (c 2.182, benzene).

Step 2

Synthesis of (−)-p-(2-cyano-2-methylhexyloxy) phenol.

While 480 mg (1.6 mM) of (+) 2-cyano-2-methylhexyl p-toluenesulfonate, 357 mg (3.2 mM) of hydroquinone and 1.5 ml of n-butanol were stirred in a nitrogen atmosphere, sodium butoxide obtained by dissolving 83.3 mM (2.1 mM) of sodium hydroxide in 2.2 ml of n-butanol was added dropwise, followed by stirring for 20 hours under heating at 120° C. After the reaction, 5 ml of saturated sodium chloride aqueous solution was added, followed by extraction with ether. The ether layer was washed with distilled water and dried on sodium sulfate, followed by distilling-off of the solvent to obtain 296 mg of a crude product, which was then purified by thine layer chromatography (developer solvent: methylene chloride) to obtain 81.3 mg of (−)-p-(2-cyano-2-methylhexyloxy)phenol (Yield: 19.1%). $[\alpha]_D$ −1.8 degree (c 0.836, benzene).

Step 3

Synthesis of (−) 4-(2′-cyano-2′-methylhexyloxy)phenyl 4-(4′-n-decyloxyphenyl)benzoate.

1 ml of thionyl chloride was added to 121 mg (0.34 mM) of 4-(4′-n-decyloxyphenyl)benzoic acid, and the mixture was heat-refluxed for 2 hours in a nitrogen atmosphere. Excessive thionyl chloride was distilled off under a reduced pressure to form an acid chloride, to which were added together 76.2 mg (0.68 mM) of triethylenediamine, 81.3 mg (0.31 mM) of (−)-p-(2-cyano-2-methylhexyloxy)phenol and 2 ml of dry benzene, followed by 2 hours of stirring under heating at 50° C. Then, 16.3 mg (0.68 mM) of sodium hydride was added thereto together with 1 ml of dry benzene, followed by 2 hours of heat-refluxing. After the reaction, the mixture was left standing for cooling to room temperature and 2 ml of 2M-hydrochloric acid was added, followed by extraction with ether. The ether layer was washed with saturated sodium chloride aqueous solution and acid on sodium sulfate, followed by distilling-off of the solvent to form 217 mg of a crude product, which was then purified by thin layer chromatography (developer solvent: hexane/methylene chloride=1/2) to obtain 71.7 mg of (−)-4-(2′-cyano-2′-methylhexyloxy)phenyl 4-(4′-n-decyloxyphenyl)benzoate (Yield: 38.6%). $[\alpha]_D$ −2.1 degrees (c 0.840, benzene). Phase transition temperature (°C.):

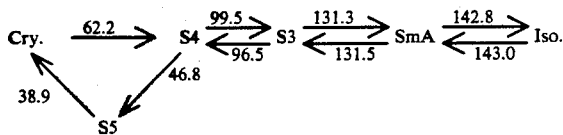

wherein S3, S4, and S5 denote smectic phases (unidentified) other than SmA and SmC*.

EXAMPLE 5

(+)-(2-cyano-2-methylhexyloxy)phenyl 4-(n-octyloxybiphenyl)-4″-carboxylate was prepared through the following steps 1)–4).

Step 1

Production of (+)-2-cyano-2-methylhexyl p-toluenesulfonate.

1.739 g (12.3 mM) of (−)-2-cyano-2-methylhexanol-$[\alpha]_D$ −0.91 degree, $[\alpha]_{435}$ −2.2 degrees (c 1.10, CH$_2$Cl$_2$)) was stirred together with 2.962 g (37.0 mM) of dry pyridine, and 2.588 g (13.6 mM) of p-toluenesulfonyl chloride was added thereto, followed by 7 hours of stirring at room temperature. After the reaction, the mixture was gradually added to 20 ml of 2N-hydrochloric acid to remove pyridine, followed by extraction with diethyl ether. The ether layer was washed with distilled water and dried on anhydrous sodium sulfate. After distilling off the solvent, the product was purified by silica gel column chromatography with the use of a mixture solvent of dichloromethane/hexane (2/1) to obtain 2.690 g of the objective product.

Yield: 70.3%
Optical rotation
$[\alpha]_{589}$ +12.8 degrees (c 1.166, benzene)
$[\alpha]_{435}$ +26.9 degrees (c 1.166, benzene)

Step 2

Production of (+)-4-(2-cyano-2-methylhexyloxyphenyl)benzyl ether.

111.0 mg (2.8 mM) of sodium hydride (60%) was placed in a round-bottomed flask and washed with a small amount of dry benzene, followed by removal of the benzene, addition of 4 ml of dry N,N-dimethylformamide instead thereof and stirring until no foaming occurred. Then, 714 mg (2.3 mM) of (+)-2-cyano-2-methylhexyl p-toluenesulfonate was added, and the mixture was stirred for 2.5 hours at 120° C. After the reaction, the solvent was distilled off, and a small amount of distilled water was added to destroy excessive sodium hydride, followed by extraction with diethyl ether. The resultant diethyl ether layer was washed with a small amount of distilled water and dried on sodium sulfate. After distilling off the solvent, the product was purified by column chromatography with a dichloromethane/hexane (2/1) mixture solvent to obtain 640 mg of the objective product.

Yield: 640 mg (86.1%)
Optical rotation:
$[\alpha]_{589}$ +3.3 degrees (c 1.152, benzene)
$[\alpha]_D$ +6.8 degrees (c 1.152, benzene)

Step 3

Production of (+)-4-(2-cyano-2-methylhexyloxy)phenol

In a round-bottomed flask, 640 mg (1.98 mM) of (+)-4-(2-cyano-2-methylhexyloxy)phenyl benzyl ether and 30 ml of ethanol were placed and well dissolved by heating at 40° C., and 200 mg of paradium/activated carbon was added thereto, followed by setting on an ordinary pressure-hydrogenation apparatus and hydrogenation with 50.8 ml of hydrogen at 40° C. After the reaction, the paradium/activated carbon was removed by filter paper, followed by distilling-off of the solvent and extraction with diethyl ether. The ether layer was washed with a small amount of distilled water and dried on sodium sulfate. After distilling off the solvent, the product was purified by silica gel column chromatography with an ethyl acetate/hexane (2/5) mixture solvent to obtain 306 mg of the objective product.

Yield: 306 mg (66.3%)
Optical rotation
$[\alpha]_{589}$ +3.4 degrees (c 1.048, benzene)
$[\alpha]_{435}$ +7.2 degrees (c 1.048, benzene)

Step 4

Production of (+)-(2-cyano-2-methylhexyloxy)phenyl 4-(n-octyloxybiphenyl)-4″-carboxylate.

In a round-bottomed flask, 88 mg (0.27 mM) of 4-(n-octyloxybiphenyl)carboxylic acid and 2 ml of thionyl chloride were placed and heat refluxed for 1.5 hours. After the reaction, excessive thionyl chloride was distilled off, and dry benzene was further added to the system and then distilled off. Thereto, 61 mg (0.54 mM) of triethylenediamine was added together with 1.5 ml of dry benzene, and then 63 mg (0.27 mM) of (+)-4-(2-cyano-2-methylhexyloxy)phenol was added, followed by 2 hours of stirring under heating at 50° C. Further, 21.8 mg (0.54 mM) of sodium hydride (60%) and 1 ml of dry benzene were added thereto, followed by 2 hours of heat-refluxing. After the reaction, the mixture was cooled to room temperature by standing, and 1N-hydrochloric acid was added little by little to remove excessive sodium hydride. The mixture was subjected to extraction with diethyl ether, and the resultant ether layer was washed with saturated sodium chloride aqueous solution and dried on sodium sulfate. After distilling off the solvent, the product was purified by silica gel column chromatography with a dichloromethane/hexane (2/1) mixture solvent and then dissolved in 0.2 ml of benzene, followed by addition of 1.0 ml of hexane for recrystallization to obtain 59 mg of the objective product.

Yield: 59 mg (40.4%)
Optical rotation
$[\alpha]_{589}$ +1.1 degree (c 0.872, CHCl$_3$)
$[\alpha]_{435}$ +3.7 degrees (c 0.872, CHCl$_3$)

EXAMPLE 6

Production of (+)-(2-cyano-2-methylhexyloxy)phenyl 4-(n-dodecyloxybiphenyl)-4"-carboxylate.

Step 4) of Example 5 was repeated by reacting 214 mg (0.56 mM) of 4-(n-dodecyloxybiphenyl)carboxylic acid instead of the 4-(n-octyloxybiphenyl)carboxylic acid with 129 mg (0.56 mM) of (+)-4-(2-cyano-2-methylhexyloxy)phenol. The crude product thus obtained was purified by thin layer chromatography for separation with a dichlorometane/hexane (5/2) mixture solvent and then dissolved with 0.3 ml of benzene, followed by addition of 2.0 ml of hexane for reprecipitation.

Yield: 147 mg (44.0%)
Optical rotation
$[\alpha]_{589}$ +1.3 degree (c 1.274, CHCl$_3$)
$[\alpha]_{435}$ +3.1 degrees
Phase transition temperature (°C.)

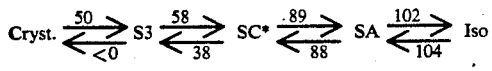

EXAMPLE 7

Production of (−)-4'-(2-cyano-2-methylhexyloxy)phenyl 4-n-decyloxybenzoate

Step 4) of Example 5 was repeated by reacting 91.8 mg (0.33 mM) of 4-n-decyloxybenzoic acid instead of the 4-(n-octyloxybiphenyl)carboxylic acid with 78.9 mg (0.3 mM) of (−)-4-(2-cyano-2-methylhexyloxy)phenol. The crude product thus obtained was purified by thin layer chromatography for separation with a dichloromethane/hexane (2/1) mixture solvent and then further by column chromatography to obtain 69.3 mg of the objective product.

Yield: 69.3 mg (44.1%)
Optical rotation
$[\alpha]_{589}$ −2.6 degrees (c 1.274, CHCl$_3$)
$[\alpha]_{435}$ −1.6 degrees (c 1.094, CHCl$_3$)
Phase transition temperature (°C.)

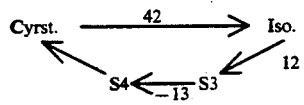

EXAMPLE 8

Production of (−)-(2-cyano-2-methylhexyloxy)phenyl 4-(5-decyl-2-pyrimidyl)benzoate Step 4) of Example 5 was repeated by reacting 101 mg (0.34 mM) of 4-(5-decyl-2-pyrimidyl)benzoic acid instead of the 4-(n-octyloxybiphenyl)carboxylic acid with 72 mg (0.30 mM) of (−)-4-(2-cyano-2-methylhexyloxy)phenol. The product thus obtained was purified by silica gel column chromatography with dichloroethane and then washed with hexane to obtain 96 mg of the objective product. Yield: 96 mg (60.7%)

Optical rotation
$[\alpha]_{589}$ −1.7 degree (c 1.362, CHCl$_3$)
$[\alpha]_{435}$ −2.8 degrees

EXAMPLE 9

(−)-4-(4"-n-octyloxy)biphenyl 4-(2-cyano-2-methylhexyloxy)benzoate was prepared through the following steps 1)-3).

Step 1

Production of (−)-ethyl 4-(2-cyano-2-methylhexyloxy)benzoate.

In a round-bottomed flask, 192.9 mg (4.8 mM) of sodium hydride (60%) was placed and washed with a small amount of dry benzene. After removing the benzene, 4 ml of dry N,N-dimethylformamide was added instead and further 664 mg (4 mM) of ethyl p-hydroxybenzoate was added, followed by stirring unit foaming ceased to occur. Then, 1244 g (4 mM) of (−)-2-cyano-2-methylhexyl p-toluenesulfonate obtained through an operation similar to Step 1) in Example 5 was added, followed by 6 hours of stirring at 120° C. After the reaction, the solvent was distilled off, and a small amount of distilled water was added to kill excessive sodium hydride, followed by extraction with diethyl ether. The ether layer was washed with a small amount of distilled water and dried on sodium sulfate. After distilling off the solvent, the product was purified by column chromatography with the use of dichloromethane as the developer solvent to obtain 890 mg of the objective product (Yield: 77.0%).

Step 2

In a round-bottomed flask with ground fitting, 890 g (3.1 mM) of (−)-ethyl 4-(2-cyano-2-methylhexyloxy)benzoate was placed, and a solution of 372 mg (9.3 mM) of sodium hydroxide in 6 ml of distilled water was added thereto, followed further by addition of 6 ml of methanol and stirring at room temperature overnight. After the reaction, the solvent was distilled off and 2N-hydrochloic acid was added to provide pH 1, followed by extraction with diethyl ether. The ether layer was washed with a small amount of distilled water and dried on sodium sulfate. After distilling off the solvent, the crude product was dissolved in 0.3 ml of benzene and 0.5 ml of hexane was added, followed by standing in a refrigerator for recrystallization to recover 707 mg of the purified product as a crystal. Yield: 707 mg (87.4%).

Optical ration
$[\alpha]_{589}$ −1.0 degree (c 1.080, acetone)
$[\alpha]_{435}$ −2.9 degrees (c 1.080, acetone)

Step 3

Production of (−)-4-(4"-n-octyloxy)biphenyl 4-(2-cyano-2-methylhexyloxy)benzoate.

In a round-bottomed flask, 157 mg (0.6 mM) of (−)-4-(2-cyano-2-methylhexyloxy)benzoic acid and 2 ml of thionyl chloride were placed and heat-refluxed for 1.5 hours, followed by distilling-off of excessive thionyl chloride, addition of dry benzene and distilling-off thereof. Then, 135 mg (1.2 mM) of triethylenediamine was added together with 2 ml of dry benzene, and 179 mg (0.6 mM) of p-n-octyloxybiphenylcarboxylic acid was added, followed by 2 hours of stirring at 50° C. Further, 48.2 mg (1.2 mM) of sodium hydride (60%) was added together with 1 ml of benzene, followed by 2 hours of heat-refluxing. After the reaction, the mixture was cooled to room temperature by standing, and 1N-hydrochloric acid was added little by little to remove excessive sodium hydride, followed by extraction with diethyl ether. The resultant ether layer was washed with saturated sodium chloride aqueous solution and dried on sodium sulfate. After distilling off the solvent, the product was purified by silica gel column chromatography with dichloroethane and recrystallized from 2 ml of ethanol to obtain the objective product. Yield: 137 mg (42.2%)

Optical rotation
[α]$_{589}$ −1.1 degree (c 1.096, CHCl$_3$)
[α]$_{435}$ −2.4 degrees

EXAMPLE 10

Production of (+)-4-(4"-n-decyloxy)biphenyl 4-(2-cyano-2-methylhexyloxy)benzoate.

153 mg (0.59 mM) of (+)-4-(2-cyano-2-methylhexyloxy)benzoic acid obtained similarly as in Steps 1) and 2) of Example 9 by using (+)-2-cyano-2-methylhexyl p-toluenesulfonate as the starting material was reacted with 192 mg (0.59 mM) of p-n-decyloxybiphenylcarboxylic acid similarly as in Step 3) of Example 9. The resultant crude product was purified by silica gel column chromatography with a dichloromethane/hexane (2/1) mixture solvent, followed by addition of 2 ml of ethanol for recrystallization to obtain 163 mg of the objective product. Yield: 163 mg (48.6%)

Optical rotation
[α]$_{435}$ +1.9 degree (c 2.38, CHCl$_3$)
Phase transition temperature (°C.)

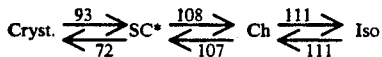

EXAMPLE 11

Production of (+)-5-n-octyl-2-{4-[4-(2-cyano-2-methylhexyloxybenzoyloxy]phenyl}pyrimidine.

183 mg (0.70 mM) of (+)-4-(2-cyano-2-methylhexyloxy)benzoic acid obtained similarly as in Steps 1) and 2) of Example 9 was reacted with 220 mg (0.70 mM) of 5-n-octyl-2-pyrimidylphenol similarly as in Step 3) of Example.

The resultant crude product was purified by silica gel column chromatography with an ethyl acetate/hexane (1/1) mixture solvent and recrystallized from ethanol to obtain 209 mg of the objective product. Yield: 208 mg (53.6%)

Optical rotation
[α]$_{589}$ −1.0 degree (c 1.001, CHCl$_3$)
[α]$_{435}$ −2.7 degrees

EXAMPLE 12

(−)-4-(4"-decyloxybiphenyl)biphenyl 4-(2-cyano-2-methylpentyloxy)benzoate was produced through the following Steps 1)-4).

Step 1

Production of (−)-2-cyano-2-methylpentyl p-toluenesulfonate.

In a round-bottomed flask, 1.35 mg (10.6 mM) of (−)-2-cyano-2-methylpentanol was dissolved in 2.52 g of dry pyridine. The mixture was placed on an ice bath, and 2.22 g (11.7 mM) of p-toluenesulfonyl chloride was added, followed by 6 hours of stirring at room temperature. After the reaction, 10 ml of 6N-hydrochloric acid was added, followed by 3 times of extraction with 15 ml of diethyl ether. The extract was dried overnight on anhydrous sodium sulfate, followed by distilling-off of the solvent and purification by column chromatography by using 80 g of silica gel and a dichloromethane/benzene (2/1) solvent to obtain (−)-2-cyano-2-methylpentyl p-toluenesulfonate. Yield: 2.57 g (9.1 mM), 86%

Optical rotation
[α]$_D$ −15.1 degrees,
[α]$_{435}$ −30.3 degrees, (c1, benzene)

Step 2

Production of (−)-ethyl p-(2-cyano-2-methylpentyloxy)benzoate.

172 mg (4.3 mM) of sodium hydride (60%) was placed in a 20 ml-round-bottomed flask with ground-fitting in a nitrogen atmosphere, and 1 ml of benzene was added, followed by 30 seconds of stirring. The sodium hydride was settled by standing, the benzene was removed by a syringe, and 4 ml of dimethylformamide was added instead. Thereto, 0.99 g (3.6 mM) of ethyl p-hydroxybenzoate was added, and the mixture was stirred until hydrogen ceased to occur. After foaming was stopped, 1.03 g (3.6 mM) of (−)-2-cyano-2-methylpentyl p-toluenesulfonate was added, followed by 6 hours of stirring at 120° C. After the reaction, the dimethylformamide was distilled off, and 5 ml of distilled water was added, followed by 3 times of extraction with 5 ml of ether. The extraction liquid was dried overnight on anhydrous sodium sulfate and purified by column chromatography by using 40 g of silica gel and dichloromethane as the solvent to obtain 7.1 g (2.6 mM) of (−)-ethyl p-(2-cyano-2-methylpentyloxy)benzoate. Yield: 71%, [α]$_D$ −2.4 degrees (c1, diethyl ether).

Step 3

Production of (−)-p-(2-cyano-2-methylpentyloxy)benzoic acid.

In a round-bottomed flask, 0.71 g (2.6 mM) of (−)-ethyl p-(2-cyano-2-methylpentyloxy)benzoate and 13 ml of pentanol were placed and stirred. An aqueous solution of 0.45 g (10.8 mM) of sodium hydroxide in 5 ml of distilled water was added thereto, followed by stirring for 22 hours at room temperature. After the reaction, methanol was distilled off under reduced pressure, and 3N-hydrochloric acid was added until pH 1. White crystal was precipitated and recovered by filtration. The crystal was dried in a desiccator and re-crystallized from a benzene/hexane mixture solvent to obtain 0.489 (1.9 mM) of the objective product.

Yield: 75%
Optical rotation
[α]$_D$ −0.5 degree,
[α]$_{435}$ −3.5 degrees, (c1, CHCl$_3$)

Step 4

Production of (−)-4-(4"-decyloxy)biphenyl 4-(2-cyano-2-methylpentyloxy)benzoate. 240 mg (0.97 mM) of (−)-p-(2-cyano-2-methylpentyloxy)benzoic acid and 2 ml of thionyl chloride were stirred for two hours under heat-refluxing at 80° C. on an oil bath. After the reaction, addition of 2 ml of dry benzene and distilling-off thereof were repeated three cycles so as to remove the thionyl chloride to the utmost. Separately, 217 mg (1.94 mM) of triethylenediamine was dissolved in 1 ml of dry benzene and dried with potassium hydroxide, and 220 mg (0.97 mM) of p-decyloxybiphenol was dissolved therein to obtain a solution, which was then added together with 4 ml of dry benzene to the above reaction system. The mixture was stirred for 2 hours at 50° C., and 46 mg (1.16 mM) of sodium hydride (60%) was added, followed by 2 hours of heat-refluxing. After the reaction, the reaction liquid was cooled by standing to room temperature, and 3N-HCl was added until pH 1. The mixture was extracted by benzene, and the benzene extract was dried on anhydrous sodium sulfate, followed by distilling-off of the solvent and purification by column chromatography by using a benzene/hexane (1/1) mixture solvent as the eluent to obtain 0.35 g (0.63 mM) of the objective product. Yield: 65%.

Optical rotation
$[\alpha]_D$ −1.0 degree,
$[\alpha]_{435}$ −0.4 degree, (c1, $CH_2Cl_2$).

EXAMPLE 13

(−)-4-(4"-octyloxy)biphenyl 4-(2cyano-2-methylpentyloxy)benzoate was obtained in the same manner as in Example 12 except that p-octyloxybiphenol was used instead of p-decyloxybiphenol in Step 4) of Example 12. Yield: 53%.

Optical rotation
$[\alpha]_D$ −0.8 degree,
$[\alpha]_{435}$ −0.2 degree, (c1, $CHCl_3$)

EXAMPLE 14

(+)-(2-cyano-2-methylpentyloxy)phenyl 4-(n-dodecyloxybiphenyl)-4"-carboxylate was produced through the following Steps 1)-3):

Step 1

Production of (+)-4-(2-cyano-2-) methylpentyloxy)phenyl benzyl ether.

Step 2) of Example 5 was repeated by using (−)-2-cyano-2-methylpentyl p-toluenesulfonate obtained in Step 1) of Example 12 instead of the (+)-2-cyano-2-methylhexyl p-toluenesulfonate used in Step 2) of Example 5 to obtain (+)-4-(2-cyano-2-methylpentyloxy)-phenyl benzyl ether. Yield: 81%.

Optical rotation
$[\alpha]_D$ +0.6 degree,
$[\alpha]_{435}$ +1.2 degree, (c1, methanol)

Step 2

Production of (+)-4-(2-cyano-2-methylpentyloxy)-phenol.

Step 3) of Example 5 was repeated by using the above-obtained (+)-4-(2-cyano-2-methylpentyloxy)-phenyl benzyl ether instead of the (+)-4-(2-cyano-2-methylhexyloxy)phenyl benzyl ether used in Step 3) of Example 5 to obtain (+)-4-(2-cyano-2-methylpentyloxy)phenol. Yield: 97%.

Optical rotation
$[\alpha]_D$ +0.8 degree,
$[\alpha]_{435}$ +2.4 degrees, (c1, benzene)

Step3

Production of (+)-(2-cyano-2-methylpentyloxy)phenyl 4-(n-dodecyloxybiphenyl)-4"-carboxylate.

In a 20 ml round-bottomed flask with ground-fitting in a nitrogen atmosphere, 382 mg (1.0 mM) of p-dodecyloxy-p"-biphenylcarboxylic acid and 2 ml of thionyl chloride were placed and stirred for 2 hours under heat-refluxing at 80° C. on an oil bath. After the reaction, an operation including addition of 2 ml of dry benzene and distilling-off of the solvent was repeated 3 cycles so as to remove the thionyl chloride to the utmost. Separately, 224 mg (2.0 mM) of triethylenediamine was dissolved in 1 ml of dry benzene and dried with potassium chloride, and (+)-p-(2-cyano-2-methylpentyloxy)phenol was dissolved to form a solution, which was then added together with 4 ml of dry benzene to the above-reaction system. The mixture was stirred for 2 hours at 50° C. After the reaction, 48 mg (1.2 mM) of sodium hydride (60%) was added together with 1 ml of dry benzene, followed by 2 hours of stirring under heat-refluxing at 80° C. After the reaction, 3N-hydrochloric acid was added until pH 1, followed by extraction with benzene. The resultant solution was dried on anhydrous sodium sulfate and the solvent was distilled-off, followed by purification by silica gel column chromatography with a dichloromethane/benzene (1/1) mixture solvent as the eluent to obtain 517 mg (0.81 mM) of the objective product. Yield: 89%

Optical rotation
$[\alpha]_D$ +0.1 degree,
$[\alpha]_{435}$ +0.7 degree (c1, $CH_2Cl_2$)

EXAMPLE 15

(+)-(2-cyano-2-methylpentyloxy)phenyl 4-(n-decyloxybiphenyl)-4"-carboxylate was prepared in the same manner as in Example 14 except that p-decyloxy-p"-biphenylcarboxylic acid was used instead of p-dodecyloxy-p"-biphenylcarboxylic acid in Step 3) of Example 14.

$[\alpha]_D$ +0.2 degree,
$[\alpha]_{435}$ +0.7 degree (c1, $CH_2Cl_2$).

EXAMPLE 16

(+)-(2-cyano-2-methylpentyloxy)phenyl 4-(n-octyloxybiphenyl)-4"-carboxylate was prepared in the same manner as in Example 14 except that p-octyloxy-p"-biphenylcarboxylic acid was used instead of p-dodecyloxy-p"-biphenylcarboxylic acid in Step 3) of Example 14.

$[\alpha]_D$ +0.1 degree,
$[\alpha]_{435}$ +0.4 degree (c1.5, $CH_2Cl_2$).

The phase transition characteristics of the mesomorphic compounds obtained in Examples 12–16 are summarized in the following Table 1.

TABLE 1

$$C_nH_{2n+1}O-\phantom{}\bigcirc\!\!-\!\!\bigcirc-Z-\bigcirc-OCH_2-\overset{CH_3}{\underset{CN}{C^*}}-C_3H_7$$

| Ex. No. | n | Z | Phase transition temperature (°C.) |
|---|---|---|---|
| 12 | 10 | −OC−<br>‖<br>O | Cryst. $\underset{78}{\overset{98}{\rightleftarrows}}$ S3 $\underset{80}{\overset{107}{\rightleftarrows}}$ SmC* $\underset{110}{\overset{111}{\rightleftarrows}}$ Ch $\underset{115}{\overset{115}{\rightleftarrows}}$ Iso. |
| 13 | 8 | −OC−<br>‖<br>O | Cryst. $\xrightarrow{107}$ SmC* $\underset{}{\overset{110}{\rightleftarrows}}$ Ch $\underset{}{\overset{120}{\rightleftarrows}}$ Iso., with S4 $\underset{77}{\leftarrow}$ Se, 55, 81 transitions |
| 14 | 12 | −CO−<br>‖<br>O | Cryst. $\underset{65}{\overset{78}{\rightleftarrows}}$ SmC* $\underset{113}{\overset{113}{\rightleftarrows}}$ SmA $\underset{137}{\overset{138}{\rightleftarrows}}$ Iso. |
| 15 | 10 | −CO−<br>‖<br>O | Cryst. $\xrightarrow{69}$ SmC* $\underset{108}{\overset{109}{\rightleftarrows}}$ SmA $\underset{140}{\overset{141}{\rightleftarrows}}$ Iso., with S3, 40, 59 transitions |
| 16 | 8 | −CO−<br>‖<br>O | Cryst. $\underset{83}{\overset{84}{\rightleftarrows}}$ SmC* $\underset{95}{\overset{94}{\rightleftarrows}}$ SmA $\underset{149}{\overset{149}{\rightleftarrows}}$ Iso. |

EXAMPLE 17

Two 0.7 mm-thick glass plates were provided and respectively coated with an ITO film to form an electrode for voltage application, which was further coated with an insulating layer of vapor-deposited SiO₂. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2 microns were dispersed on one of the glass plates, the two glass plates were applied to each other with a bonding sealing agent (Lixon Bond available from Chisso K.K.) so that their rubbed directions were parallel to each other and heated at 100° C. for 60 min. to form a blank cell. The cell gap was found to be about 2 microns as measured by a Berek compensator.

Then, a liquid crystal composition was prepared by mixing a mesomorphic compound A shown below prepared by Example 1 and ferroelectric liquid crystal compounds B and C also shown below respectively in the indicated amounts, heated into an isotropic uniform mixture liquid and injected into the above-prepared cell followed by cooling from the isotropic phase down to 25° C. at a rate of 5° C./hour to prepare a ferroelectric liquid crystal device.

Compound A (Example 1)

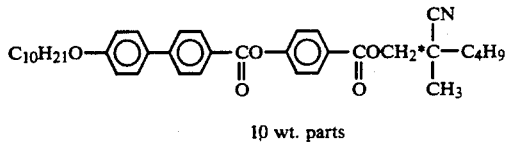

10 wt. parts

Compound B

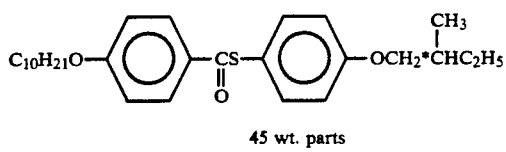

45 wt. parts

Compound C

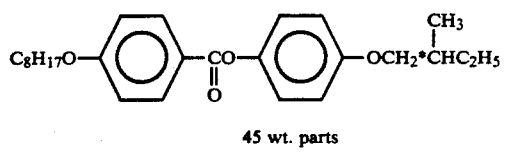

45 wt. parts

The ferroelectric liquid crystal device was subjected to measurement of an optical response time (time from voltage application until the transmittance change reaches 90% of the maximum under the application of a peak-to-peak voltage Vpp of 20V in combination with right-angle cross-nicol polarizers). The results are shown in the following Table 2.

TABLE 2

| Temp. (°C.) | Response time |
|---|---|
| 35 | 1210 usec |
| 45 | 790 |
| 55 | 600 |

COMPARATIVE EXAMPLE 1

A ferroelectric liquid crystal device was prepared in the same manner as in Example 17 except that the mesomorphic compound A used in Example 17 was not added to the ferroelectric liquid crystals and the optical response time thereof was measured. The results are shown below.

TABLE 3

| Temp. (°C.) | Response time |
|---|---|
| 35 | 1500 |
| 45 | 1000 |
| 55 | 800 |

EXAMPLE 18

A glass substrate provided with an ITO transparent electrode film was coated with a polyimide resin precursor (SP-510, mfd. by Toray K.K.), followed by heating at 300° C. for 60 min. to form a polyimide film. Then, the film was orientation-treated by rubbing. Two glass substrates thus treated were fixed to each other so that their rubbing treated axes crossed each other at right angles, thereby to form a blank cell with a cell gap of 8 microns. The cell was filled with a nematic liquid crystal composition (Lixon GR-63, a biphenyl liquid crystal mixture available from Chisso K.K.) to form a TN (twisted nematic)-type cell. When observed through a polarizing microscope, the TN-type cell showed a fringe pattern due to occurrence of reverse domain.

A liquid crystal composition was prepared by adding 1 wt. part of the optically active compound obtained by the above Example 2 to 99 wt. parts of the above Lixon GR-63 and used for preparation of a TN cell in the same manner as above. As a result of observation through a polarizing microscope, no reverse domain was observed but a uniform nematic phase was observed in the TN cell. From this fact, the mesomorphic compound of the invention was found to be effective for prevention of reverse domain.

As described above, the mesomorphic compound according to the present invention is characterized by being capable of changing its molecular chain length and provides a liquid crystal composition having an increased spontaneous polarization when contained therein. Further, a liquid crystal device using such a liquid crystal composition shows a quite fast response speed and can suppress the occurrence of reverse domain.

What is claimed is:

1. A mesomorphic compound represented by the formula:

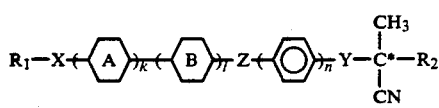 [I]

wherein $R_1$ denotes an alkyl group having 1-16 carbon atoms; $R_2$ denotes an alkyl group having 2-10 carbon atoms; X denotes a single bond or —O—; Y denotes —OCH$_2$—, Z denotes a single bond,

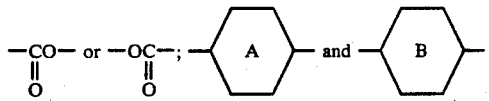

independently denote

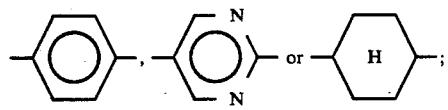

k, l and n are independently 0, 1 or 2 satisfying the relation of k+l+n=2 or 3 wherein Z is a single bond when n=0; C* denotes an asymmetric carbon atom.

2. A mesomorphic compound according to claim 1, which is

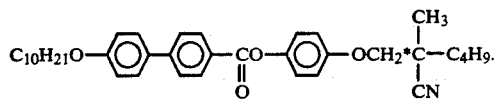

3. A mesomorphic compound according to claim 1, which is

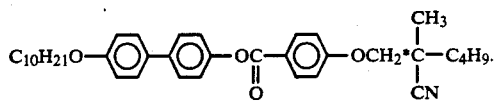

4. A mesomorphic compound according to claim 1, which is

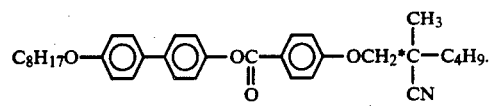

5. A mesomorphic compound according to claim 1, which is

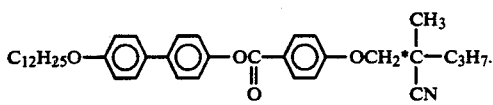

6. A mesomorphic compound according to claim 1, which is

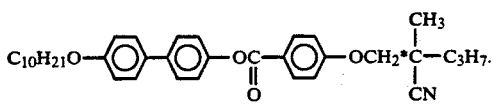

7. A mesomorphic compound according to claim 1, which is

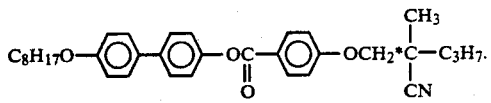

8. A mesomorphic compound according to claim 1, which is

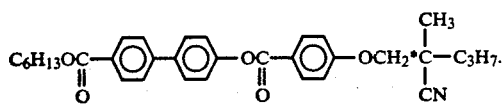

9. A mesomorphic compound according to claim 1, which is

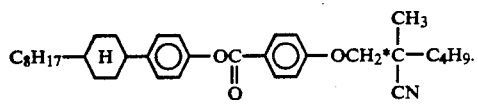

10. A mesomorphic compound according to claim 1, which is

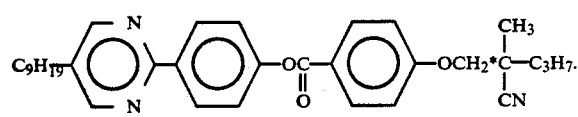

11. A mesomorphic compound according to claim 1, which is

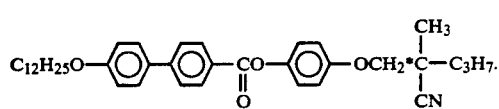

12. A mesomorphic compound according to claim 1, which is

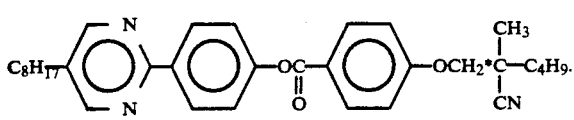

13. A mesomorphic compound according to claim 1, which is

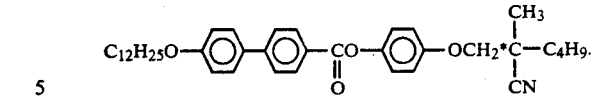

14. A mesomorphic compound according to claim 1, which is

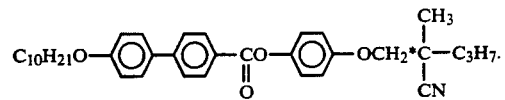

15. A mesomorphic compound according to claim 1, which is

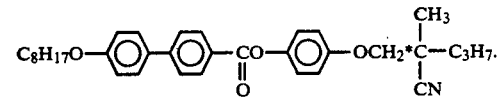

16. A mesomorphic compound according to claim 1, which is

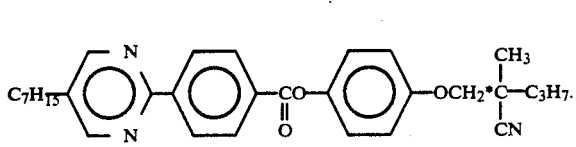

17. A mesomorphic compound according to claim 1, which is

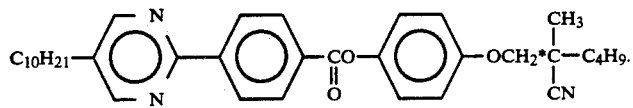

18. A mesomorphic compound according to claim 1, which is

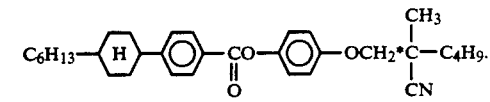

19. A mesomorphic compound according to claim 1, which is

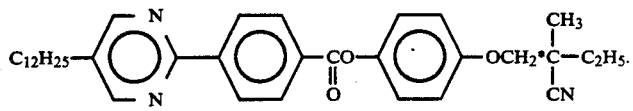

20. A mesomorphic compound according to claim 1, which is

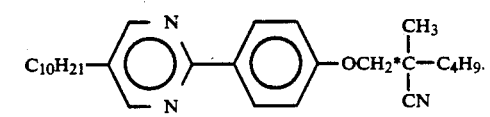

21. A mesomorphic compound according to claim 1, which is

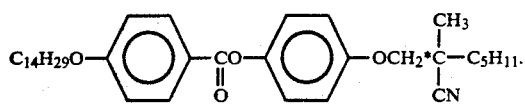

22. A mesomorphic compound according to claim 1, which is

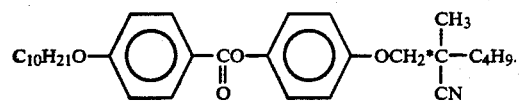

23. A mesomorphic compound according to claim 1, which is

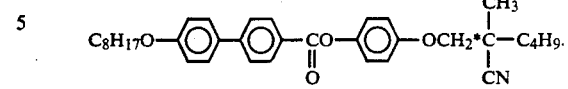

24. A chiral smectic liquid crystal composition, comprising at least two mesomorphic compounds including a mesomorphic compound represented by the formula [1] according to claim 1.

25. A liquid crystal device, comprising: a pair of substrates and a chiral smectic liquid crystal composition according to claim 24 disposed between the substrates.

* * * * *

UNITED STATES PATENT AND TRADEMARK OFFICE
CERTIFICATE OF CORRECTION

PATENT NO. : 5,075,031

DATED : December 24, 1991

INVENTOR(S) : HIROYUKI NOHIRA ET AL.   Page 1 of 3

It is certified that error appears in the above-identified patent and that said Letters Patent is hereby corrected as shown below:

TITLE PAGE:
AT [56] REFERENCES CITED

U.S. Patent Documents,
      "4,592,856" should read --4,592,858-- and
      "4,820,939" should read --4,820,839--.

Foreign Patent Documents,
      "63-104949  4/1988" should read --63-104949  5/1988--
      and "8705017  8/1988" should read --8705017  8/1987--.

Insert, --Other Publications,
      Taniguchi, H. et al., Japan. J. Appl. Phys.,
      Vol. 26, Suppl. 26-2, pp. 101-103 (1987).
      Huppatz, John L. et al., Pestic. Sci.,
      Vol. 13 (1), pp. 78-84 (1982).
      Cas, Registry Nos. 82295 - (41-8), (40-7),
      (38-3), (37-2), 1982.--.

COLUMN 4

Line 40, "$R_1\text{-}(A)_1\text{-}(B)_1\text{-}OH$" should read
   --$R_1\text{-}(A)_k\text{-}(B)_1\text{-}OH$--.

UNITED STATES PATENT AND TRADEMARK OFFICE
CERTIFICATE OF CORRECTION

PATENT NO. : 5,075,031

DATED : December 24, 1991

INVENTOR(S) : HIROYUKI NOHIRA ET AL.

It is certified that error appears in the above-identified patent and that said Letters Patent is hereby corrected as shown below:

COLUMN 5

Line 25, "$R_1\!-\!X\!-\!(A)_{\overline{1}}\!-\!(B)_{\overline{1}}\!-\!\overset{\overset{O}{\|}}{C}Cl$" should read --$R_1\!-\!X\!-\!(A)_{\overline{k}}\!-\!(B)_{\overline{1}}\!-\!\overset{\overset{O}{\|}}{C}Cl$--.

Line 57, "$R_1\!-\!X\!-\!(A)_{\overline{1}}\!-\!(B)_{\overline{1}}\!-\!OH$" should read --$R_1\!-\!X\!-\!(A)_{\overline{k}}\!-\!(B)_{\overline{1}}\!-\!OH$--.

COLUMN 13

Line 67, "4-hexyloxypenyl" should read
--4-hexyloxyphenyl--.

COLUMN 14

Line 42, "4"-carboxylate" should read --4'-carboxylate--.

COLUMN 17

Lines 21-22, "$\underset{128.9}{\overset{127.2}{\rightleftarrows}}$ Iso." should read --$\underset{127.2}{\overset{128.9}{\rightleftarrows}}$ Iso.--.

UNITED STATES PATENT AND TRADEMARK OFFICE
CERTIFICATE OF CORRECTION

PATENT NO. : 5,075,031
DATED : December 24, 1991
INVENTOR(S) : HIROYUKI NOHIRA ET AL.

It is certified that error appears in the above-identified patent and that said Letters Patent is hereby corrected as shown below:

COLUMN 19

Lines 33-34, "$\underset{143.0}{\overset{142.8}{\rightleftarrows}}$ Iso." should read --$\underset{142.8}{\overset{143.0}{\rightleftarrows}}$ Iso.--.

COLUMN 21

Line 24, "dichlorometane" should read --dichloromethane--.

COLUMN 22

Line 55, "optical ration" should read --optical rotation--.

COLUMN 30

Line 4, "—OCH$_2$—," should read ---OCH$_2$—;--.

Signed and Sealed this

Twenty-first Day of November, 1995

Attest:

BRUCE LEHMAN

Attesting Officer   Commissioner of Patents and Trademarks